United States Patent [19]

Kraus

[11] Patent Number: 5,478,944
[45] Date of Patent: Dec. 26, 1995

[54] PROCESS FOR THE PREPARATION OF 2-AMINO-5-AMINOMETHYL-PYRIDINE

[75] Inventor: Helmut Kraus, Köln, Germany

[73] Assignee: Bayer Aktiengesellschaft, Leverkusen, Germany

[21] Appl. No.: 179,784

[22] Filed: Jan. 11, 1994

[30] Foreign Application Priority Data

Jan. 18, 1993 [DE] Germany .................. 43 01 110.1

[51] Int. Cl.⁶ .............. C07D 213/09; C07D 211/02; C07D 413/04; C07D 403/04
[52] U.S. Cl. ............. 546/250; 546/289; 546/193; 544/124; 544/360
[58] Field of Search ................... 546/250, 289, 546/193; 544/124, 360

[56] References Cited

U.S. PATENT DOCUMENTS

| | | | |
|---|---|---|---|
| 3,632,807 | 1/1972 | Maurer et al. ............. | 546/345 |
| 4,404,388 | 9/1983 | Fäh et al. ................. | 546/345 |
| 4,405,552 | 9/1983 | Miesel ..................... | 514/348 |
| 4,678,795 | 7/1987 | Shiokawa et al. ........... | 514/341 |
| 4,738,924 | 4/1988 | Kulla et al. ............... | 435/121 |
| 4,774,247 | 9/1988 | Shiokawa et al. ........... | 514/256 |
| 4,812,571 | 3/1989 | Shiokawa et al. ........... | 546/296 |
| 5,010,201 | 4/1991 | Kaufmann et al. ........... | 546/316 |

FOREIGN PATENT DOCUMENTS

| | | | |
|---|---|---|---|
| 0060071 | 9/1982 | European Pat. Off. ....... | 514/348 |
| 0376279 | 7/1990 | European Pat. Off. ....... | 546/309 |

OTHER PUBLICATIONS

J. Org. Chem., vol. 29, 1964, pp. 1800–1808; "The Synthesis and Reactions of β–Chloroacrylonitrile", F. Scotti et al.
1962 Interscience Publishers, Erwin Klingsberg, "Pyridine and its derivatives, Part Three" cover page ' pp. 68–69; Oct. 29, 1973.

Science, American Association for the Advancement of Science, Oct. 3, 1969, vol. 166, No. 3901; "Photochemical Reactions and the Chemical Evolution of Purines and Nicotinamide Derivatives"; cover page + pp. 765–766 (Nov. 7, 1969).

*Primary Examiner*—Alan L. Rotman
*Attorney, Agent, or Firm*—Sprung Horn Kramer & Woods

[57] ABSTRACT

2-Amino-5-aminomethyl-pyridine, of the formula

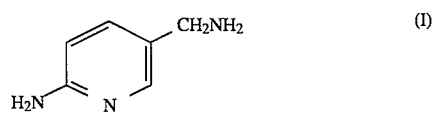

can be prepared by reacting substituted methylene-glutaconic acid dinitrile of the formula

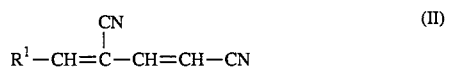

having the meaning of $R^1$ as given in the general description, at from 50° to 200° C., initially with from 3 to 20 mol of ammonia and then, in the presence of a hydrogenation catalyst, with hydrogen. The hydrogen is present an a partial pressure of from 10 to 250 bar. The reaction can be carried out with or without solvent.

11 Claims, No Drawings

PROCESS FOR THE PREPARATION OF 2-AMINO-5-AMINOMETHYL-PYRIDINE

The invention relates to a process for the preparation of 2-amino-5-aminomethyl-pyridine by reacting methyleneglutaconic acid dinitriles with ammonia and hydrogen in the presence of a hydrogenation catalyst in a "one-pot" reaction which may optionally be carried out in a solvent as reaction medium. 2-Amino-5-aminomethyl-pyridine (AAMP) is an important intermediate in the synthesis of insecticides of the nitromethylene class (EP 163 855, EP 376 279).

The preparation of suitable 2,5-disubstituted pyridines from which the above key compounds are accessible is technically difficult. For instance, 6-chloronicotinic acid, whose side chain would have to be functionalized further, is only accessible by bacterial hydroxylation and subsequent chlorination (EP 152 949, EP 72 777). 2-Chloro-5-methylpyridine, whose methyl group is difficult to chlorinate, can be prepared by halogenating picoline N-oxide (German Offenlegungsschrift 38 39 332) or from 2-amino-5-methylpyridine (German Auslegeschrift 16 95 659). The halogenation of the N-oxide and the amination of β-picoline are, however, in each case hampered by the problem of the formation of unwanted isomers, which leads to technically laborious processes and burdensome separating operations.

In the light of this prior art, it was surprising that AAPM can be prepared in a technically simple manner and in high yield free from isomers, starting from an easily accessible $C_6$ aliphatic component. The molecule which is eliminated during the cyclization, for example a secondary amine, surprisingly does not lead to any impairment in the conduct of the reaction. Despite the highly nucleophilic nature of a secondary amine of this type towards ammonia, the proportion of tertiary amine is distinctly below the quantities to be expected from statistical calculations.

The invention therefore relates to a process for the preparation of 2-amino-5-aminomethyl-pyridine, of the formula

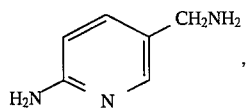
(I)

which is characterized in that a substituted methyleneglutaconic acid dinitrile of the formula

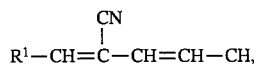
(II)

in which $R^1$ represents $—OR^2$ or $—N(R^2,R^3)$, in which $R^2$ and $R^3$, independently of one another, present straight-chain or branched $C_1–C_8$-alkyl, $C_3–C_8$-alkenyl, $C_2–C_8$-alkoxyalkyl, $C_4–C_8$-alkoxyalkenyl, $C_3–C_8$-cycloalkyl, $C_6–C_{12}$-aryl, $C_7–C_{10}$-aralkyl or a 5- to 8-membered saturated or unsaturated heterocyclic ring containing 1 or 2 hetero atoms from the group comprising N, O and S, in which case $R^2$ and $R^3$ may in addition, together with the N atom on which they are substituents, form a 5- to 8-membered ring which may contain a further hetero atom from the group comprising N, O and S, is initially reacted at from 50° to 200° C., preferably from 60° to 150° C., with from 3 to 200 mol, preferably from 5 to 100 mol, of ammonia and then reacted in the presence of a hydrogenation catalyst with hydrogen which is present at a $H_2$ partial pressure of from 10 to 250 bar, preferably from 20 to 200 bar, the reaction being carried out with or without solvent.

Straight-chain or branched $C_1–C_8$-alkyl is, for example, methyl, ethyl, propyl, isopropyl, butyl, isobutyl, tert-butyl, the isomeric pentyls, hexyls and octyls, and preferably the $C_1–C_4$-alkyl radicals mentioned.

Straight-chain or branched $C_3–C_8$-alkenyl is, for example, allyl, the isomeric butenyls, pentenyls, hexenyls or octenyls, and preferably the $C_3–C_4$-alkenyl radicals mentioned.

Straight-chain or branched $C_2–C_8$-alkoxyalkyl is, for example, methoxymethyl, ethoxymethyl and further radicals from the group comprising $C_3–C_9$-alkyl in which one $CH_2$ group is replaced by an O atom.

Straight-chain or branched $C_4–C_8$-alkoxyalkenyl is, for example, methoxyallyl, 2-methoxy-propenyl and others from the group comprising $C_4–C_9$-alkenyl in which a $CH_2$ group is replaced by an O atom.

$C_3–C_8$-cycloalkyl is, for example, cyclopropyl, methyl-cyclopropyl, dimethyl-cyclopropyl, cyclobutyl, methyl-cyclobutyl, cyclopentyl, methyl-cyclopentyl, cyclohexyl, methyl-cyclohexyl, dimethyl-cyclohexyl, cycloheptyl or cyclooctyl, and preferably cyclopropyl, cyclopentyl and cyclohexyl and their methyl or dimethyl derivatives.

$C_6–C_{12}$-aryl is, for example, phenyl, naphthyl or biphenylyl, preferably phenyl.

$C_7–C_{10}$-aralkyl is, for example, benzyl, 1-phenylethyl, 2-phenylethyl and further radicals of this type which are known to those skilled in the art, preferably benzyl.

5- to 8-membered saturated or unsaturated heterocyclic rings containing 1 or 2 hetero atoms from the group comprising N, O and S and which may be mentioned are: pyrrole, furan, thiophene, pyrrolidine, pyrazole, imidazole, thiazole, oxazole, pyridine, pyrimidine, piperazine, which can be substituted on the N atom by $C_1–C_4$-alkyl or by hydroxy-$C_1–C_4$-alkyl, morpholine, pyran, azepin, azocine, isoxazole, isothiazole, pyridazine and pyrazine. It is known to those skilled in the art that unsaturated heterocyclic rings can have a more or less pronounced aromatic character. Those saturated or unsaturated heterocyclic rings which can be mentioned preferentially are morpholine, pyrrolidine and piperidine which may be substituted by $C_1–C_4$-alkyl or by hydroxy-$C_1–C_4$-alkyl.

In addition, $R^2$ and $R^3$ together with the N atom on which they are substituents may form a 5- to 8-membered saturated or unsaturated ring which may contain a further hetero atom from the group comprising N, O and S. Examples of such rings are the heterocycles mentioned above.

In the process according to the invention, it is preferred to employ enamines in which the place of $R^2$ and $R^3$ is taken by the substituents $R^{12}$ and $R^{13}$ which, independently of one another, denote straight-chain or branched $C_1–C_8$-alkyl, cyclopropyl, cyclopentyl, cyclohexyl, phenyl or benzyl, in which case $R^{12}$ and $R^{13}$, together with the N atom on which they are substituents, may additionally form a 5- to 8-membered ring which may contain a further hetero atom from the group comprising N, O and S.

In the process according to the invention it is particularly preferred to employ enamines in which the place of $R^{12}$ and $R^{13}$ is taken by the substituents $R^{22}$ and $R^{23}$ which, independently of one another, denote $C_1–C_4$-alkyl, in which case $R^{22}$ and $R^{23}$, together with the N atom on which they are substituents, additionally denote morpholine, pyrrolidine or piperidine which may be substituted by $C_1–C_4$-alkyl or by hydroxy-$C_1–C_4$-alkyl.

It is preferred for the place of $R^1$ to be taken by the substituent $R^{11}$ having the meaning $—N(R^2,R^3)$, in which $R^2$ and $R^3$, independently of one another, have the meaning given above.

The reaction in the process according to the invention may be carried out in excess ammonia. It is possible, in addition, for a solvent to be employed as reaction medium. Suitable solvents are individual members or a mixture thereof from the groups comprising hydrocarbons, halogenated hydrocarbons, tertiary amines, ketones, nitriles, dialkylcarboxamides, ethers, phosphoric acid peralkylamides, sulphonic acid dialkylamides, N-alkyl-lactams, peralkyl-ureas, dialkyl sulphoxides, dialkyl sulphones and alcohols. Examples of such solvents, in a list which is by no means exhaustive, are: petroleum ether, toluene, xylene, cyclohexane, chlorobenzene, ligroin, triethylamine, anisole, methyl tert-butyl ether, dimethylformamide, acetamide, N-methyl-pyrrolidone, N-methyl-caprolactam and tetramethylurea. A small proportion of water in the reaction medium is not a problem.

The reaction temperature is within the range from 50° to 200° C., preferably from 60° to 150° . The quantity of ammonia is from 3 to 200 mol, preferably from 5 to 100 mol, based on the methylene-glutaconic acid dinitrile. It is preferred to work in the upper part of this range when the reaction is to be carried out without additional solvent, and vice versa.

Hydrogen is present in the reaction mixture in excess and with a $H_2$ partial pressure of from 10 to 250 bar, preferably from 20 to 200 bar.

The reaction time is dependent on various parameters such as the batch size, the temperature, the molar ratio, the hydrogen pressure and the hydrogenation catalyst and is, for instance, from 0.5 to 10 hours, preferably from 0.5 to 6 hours. Suitable hydrogenation catalysts are those based on nickel and cobalt and on the noble metals Pd, Pt and Rh, preferably Ni and Co, which may be provided in a manner familiar to those skilled in the art with dopants, such as MgO, $B_2O_3$, $TiO_2$, $V_2O_5$, $Cr_2O_3$ et cetera. Catalysts of this kind may be disposed on supports such as $SiO_2$, $Al_2O_3$, coal, zeolites and other supports known to those skilled in the art. However, nickel and cobalt catalysts can also be used without supports, for example in the form of the "skeleton" catalysts of the Raney type.

The process according to the invention can be carried out in one reactor without intermediate isolation. In this procedure the methylene-glutaconic acid dinitrile is initially reacted with ammonia, optionally in the presence of one of the solvents mentioned, and then further treated with hydrogen. The hydrogenation catalyst can be added between the reaction with ammonia and the further treatment with hydrogen; however, in a manageable and hence preferred manner it can be added even prior to the reaction with ammonia.

The process according to the invention can be represented, for example, as follows:

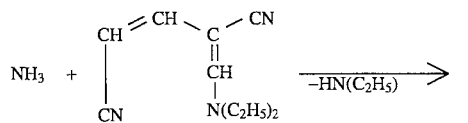

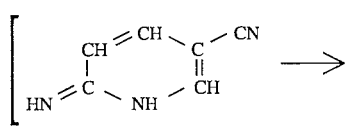

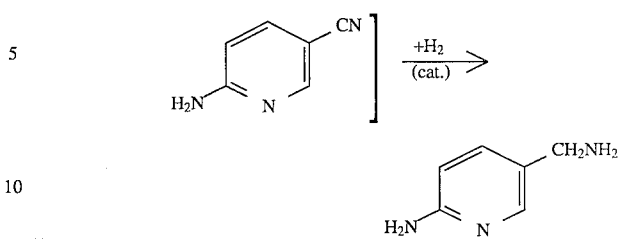

Diethylaminomethylene-glutaconic acid dinitrile reacts with ammonia, with cyclization, to give nicotinonitrile, which is then hydrogenated to give 2-amino-5-aminomethyl-pyridine.

The methylene-glutaconic acid dinitrile employed is obtainable, for example, by reacting glutaconic acid dinitrile with o-esters or o-amides. In addition, aminomethylene-glutaconic acid dinitriles can be obtained in a technically simple manner by dimerization of the β-amino-acrylonitriles on which they are based.

EXAMPLES

Example 1

15 g of dimethylaminomethylene-glutaconic acid dinitrile, 75 ml of toluene and 3 g of Ra-Ni were placed in a 0.3 l V4A stainless steel autoclave, and 25 g of gaseous ammonia were injected. The apparatus was heated to 100° C. and, after 2 h, an additional 100 bar of hydrogen were injected (117 bar total pressure). After a further 5 h, the mixture was left to cool down and the apparatus was let down. After addition of methanol, the reaction mixture was removed from the autoclave, the catalyst was isolated by filtration, and the remaining mixture was concentrated.

12.7 g of 94.2% pure product were obtained, corresponding to 95.3% of the theoretical yield.

The content of 2-amino-5-dimethylaminomethyl-pyridine was 1.3%.

$^1$H-NMR (d-DMSO) 1.4-s.0 ppm (bs, 2H, $NH_2$), 3.2–3.6 ppm (s, 2H, $NH_2$), 5.68 ppm (s, 2H, $CH_2$), 6.39 ppm (d, 1H, $H^3$), 7.38 ppm (dd, 1H, $H^4$), 7.82 ppm (d, 1H, $H^3$).

Example 2

15 g of glutaconic acid dinitrile and 3 g of Ra-Ni were initially taken analogously to Example 1, and 70 g of gaseous ammonia were injected. After 2 h at 100° C., an additional 100 bar of $H_2$ pressure was injected (total pressure: 112.8 bar) and hydrogenation was carried out for 4½ h. After the contents had cooled down and the apparatus had been let down, the mixture was taken up in methanol, the catalyst was isolated by filtration, and the mixture which remained was concentrated. 12.5 g of 95.9% pure product were obtained, corresponding to 95.6% of the theoretical yield. The proportion of dimethylamino product was 0.6%.

Example 3

Analogously to Example 1, 15 g of dinitrile with 30 ml of toluene and 10 g of ammonia were cyclized and hydrogenated. The yield was 91.3% of theory.

Example 4

15 g of diethylaminomethylene-glutaconic acid dinitrile were admixed with 3 g of Ra-Ni and 30 g of ammonia and hydrogenated at 100° C. to constant pressure. 2-Amino-5-amino-methylpyridine was obtained in 93.7% of the theoretical yield.

Example 5

15 g of ethoxymethylene-glutaconic acid dinitrile, 100 ml of toluene and 3 g of Ra-Ni were initially taken, and 30 g of gaseous ammonia were injected. After conducting further reaction analogously to Example 1, 2-amino-5-aminomethylpyridine was obtained in 86.3% of the theoretical yield.

I claim:

1. A process for the preparation of 2-amino-5-aminomethyl-pyridine, of the formula

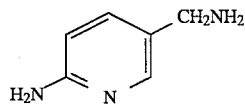

wherein a substituted methylene-glutaconic acid dinitrile of the formula

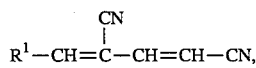

in which
R¹ represents —OR² or —N(R²,R³),
in which
R² and R³, independently of one another, present straight-chain or branched $C_1$–$C_8$-alkyl, $C_3$–$C_8$-alkenyl, $C_2$–$C_8$-alkoxyalkyl, $C_4$–$C_8$-alkoxyalkenyl, $C_3$–$C_8$-cycloalkyl, $C_6$–$C_{12}$-aryl, $C_7$–$C_{10}$-aralkyl or R² and R³, together with the N atom on which they are substituents, form a 5- to 6-membered ring wherein said rings are pyrrolidine, piperazine, morpholine, or piperidine wherein said piperazine, piperidine, morpholine and pyrrolidine moieties are optionally substituted on the N atom by $C_1$–$C_4$-alkyl or by hydroxy-$C_1$–$C_4$-alkyl, is initially reacted at a temperature from 50° to 200° C., with from 3 to 200 mol of ammonia and then reacted in the presence of a hydrogenation catalyst containing Ni, Co, Pd, Pt and Rh with hydrogen which is present at a $H_2$ partial pressure of from 10 to 250 bar, optionally in the presence of a solvent.

2. The process according to claim 1, wherein R¹ is —N(R²,R³).

3. The process according to claim 1, wherein R² and R³, independently of one another, denote straight-chain or branched $C_1$–$C_8$-alkyl, cyclopropyl, cyclopentyl, cyclohexyl, phenyl or benzyl.

4. The process according to claim 3, wherein R² and R³, independently of one another, denote $C_1$–$C_4$-alkyl or, together with the N atom, form a morpholine, pyrrolidine or piperidine ring which is optionally substituted by $C_1$–$C_4$-alkyl or by hydroxy-$C_1$–$C_4$-alkyl.

5. The process according to claim 1, wherein the solvent is a hydrocarbon, halogenated hydrocarbon tertiary amine, ketone, nitrile, dialkyl carboxamide, N-alkyl-lactam, peralkyl-urea, dialkyl sulphoxide, dialkyl sulphone, ether, alcohol, phosphoric acid peralkylamide or sulphonic acid dialkylamide.

6. The process according to claim 1, wherein the hydrogenation catalyst employed is a Raney Ni or Raney Co catalyst.

7. The process according to claim 5, wherein the solvent is selected from the group consisting of petroleum ether, toluene, xylene, cyclohexane, chlorobenzene, ligroin, triethylamine, anisole, methyl tert-butyl ether, dimethylformamide, acetamide, N-methyl-caprolactam, N-methylpyrrolidone and tetramethylurea.

8. The process according to claim 1, wherein the temperature range is from 60° to 150° C.

9. The process according to claim 1, wherein from 5 to 100 mol of ammonia are used.

10. The process according to claim 1, wherein the catalysts are MgO, $B_2O_3$, $TiO_3$, $V_2O_5$, or $Cr_2O_3$.

11. The process according to claim 1, wherein the partial pressure is from 20 to 200 bar.

* * * * *